(12) United States Patent
DeLuke

(10) Patent No.: US 7,011,518 B2
(45) Date of Patent: Mar. 14, 2006

(54) CONTOURED PALATAL EXPANDER

(76) Inventor: Anthony G. DeLuke, 5043 Forest Rd., Lewiston, NY (US) 14092

( * ) Notice: Subject to any disclaimer, the term of this patent is extended or adjusted under 35 U.S.C. 154(b) by 114 days.

(21) Appl. No.: 10/187,546

(22) Filed: Jul. 1, 2002

(65) Prior Publication Data

US 2003/0049581 A1    Mar. 13, 2003

Related U.S. Application Data

(60) Provisional application No. 60/302,566, filed on Jul. 2, 2001.

(51) Int. Cl.
    *A61C 3/00*         (2006.01)
(52) U.S. Cl. .......................................................... 433/7
(58) Field of Classification Search ................... 433/7, 433/18, 6
    See application file for complete search history.

(56) References Cited

U.S. PATENT DOCUMENTS

| | | | | |
|---|---|---|---|---|
| 4,348,179 A | * | 9/1982 | Nardella ......................... | 433/7 |
| 5,242,304 A | * | 9/1993 | Truax et al. ................... | 433/177 |
| 5,718,575 A | * | 2/1998 | Cross, III ...................... | 433/6 |
| 6,302,687 B1 | * | 10/2001 | King .............................. | 433/7 |
| 6,572,372 B1 | * | 6/2003 | Phan et al. .................... | 433/6 |
| 2004/0009449 A1 | * | 1/2004 | Mah et al. ...................... | 433/7 |

FOREIGN PATENT DOCUMENTS

| | | | | |
|---|---|---|---|---|
| DE | 352360 | * | 4/1922 | ..................... 433/7 |
| FR | 831155 | * | 5/1938 | ..................... 433/7 |
| FR | 1164740 | * | 10/1958 | ..................... 433/7 |
| GB | 641139 | * | 8/1948 | ..................... 433/7 |

* cited by examiner

*Primary Examiner*—Cary E. O'Connor
(74) *Attorney, Agent, or Firm*—Hodgson Russ LLP

(57) ABSTRACT

An orthodontic palatal expander appliance comprising an expansion screw, extensions leading from opposite ends of the expansion screw and contoured tooth engaging portions fixed to the ends of the extensions and being entirely of thermoplastic material and being shaped to conform to and grasp selected ones of a patient's teeth. The buccal, linqual and occlusal surfaces are completely covered by the thermoplastic material. The material is trimmed carefully to match the gingival contour around each tooth. The inner tooth contacting surface of each contoured tooth engaging portion is abrasively etched by means of a pressurized spray of micron-size abrasive particles. A physically bonding orthodontic adhesive, such a resin modified glass ionomer adhesive, is applied to the abrasively etched surfaces to releasably bond the contoured tooth engaging portions to the patient's teeth.

17 Claims, 5 Drawing Sheets

CONTOURED PALATAL EXPANDER

CROSS REFERENCE TO A RELATED APPLICATION

Applicant hereby claims priority based on U.S. Provisional Patent Application No. 60/302,566 filed Jul. 2, 2001 and entitled "Improved Palatal Expander" which is incorporated herein by reference.

BACKGROUND OF THE INVENTION

This invention relates to dental and orthodontic appliances, and more particularly to a new and improved palatal expander and method of making and using the same.

Palatal sutural expansion is the first treatment objective in an increasing number of orthodontic treatment plans. The need for expansion is clearly apparent in patients with posterior crossbite. Patients being prepared for mandibular advancement and patients with equal maxillary and mandibular transverse deficiency also are candidates for expansion. Such expansion is provided by an orthodontic appliance known as a palatal expander.

A variety of screw-type dental palatal expanders are commonly available and have been for decades. Previous designs include the following. Banded palatal expanders are comprised of an expansion screw which is anchored to 2 or 4 teeth (usually the first maxillary bicuspids and first maxillary molars). The metal expansion screw is soldered to stainless steel bands which have been pre-fitted to selected teeth. These bands are lined with adhesive and the entire appliance is positioned with all bands sliding gingivally along their respective teeth until the teeth are fully covered. Examples of banded palatal expanders are shown in U.S. Pat. Nos. 3,977,082 and 5,133,659, the disclosures of which are hereby incorporated by reference.

Bonded palatal expanders incorporate a frame work of heavy reinforcement metal rod material (0.036 inch to 0.040 inch rod) which is hand shaped to follow the lingual gingival margin and buccal gingival margin of all teeth to be covered. The expansion screw is soldered to this metal framework. Acrylic is applied in a powder and liquid mixture by hand to this framework and expansion screw. This acrylic is cured, trimmed and polished. This appliance is bonded onto the teeth to be covered after etching of the enamel. Common bonding adhesive similar to that used to place braces is used to coat the inside of the acrylic "cap" and placed over the anchor teeth.

Removable palatal expanders have wire clasps shaped to grip anchor teeth with an expansion screw embedded into acrylic which acts as the "body" of the appliance. The clasps are spring-like and grip onto teeth to retain the appliance.

SUMMARY OF THE INVENTION

The improved bonded palatal expander of the present invention has differences in fabrication and design as well as in the cementation technique and removal technique, as compared to prior art palatal expanders. No metal framework wrapping around all the anchor teeth exists whatsoever. Whereas the prior art design incorporates two metal components (body framework and expansion screw which were soldered together during fabrication), the improved design only incorporates the expansion screw. In particular, the improved palatal expander of the present invention comprises an expansion screw portion and tooth-engaging portions at opposite ends of the expansion screw portion, the teeth engaging portions being entirely of plastic material and shaped to conform to and grasp selected ones of the patient's teeth. The invention also includes an improved cementation technique in releasably bonding the tooth-engaging portions to the patient's teeth.

The following detailed description of the invention when read in conjunction with the accompanying drawings, is in such full, clear, concise and exact terms as to enable any person skilled in the art to which it pertains, or with which it is most nearly connected, to make and use the same. The foregoing and additional advantages and characterizing features of the present invention will become clearly apparent upon a reading of the ensuing detailed description together with the included drawing.

DETAILED DESCRIPTION OF THE INVENTION

Figure 1:
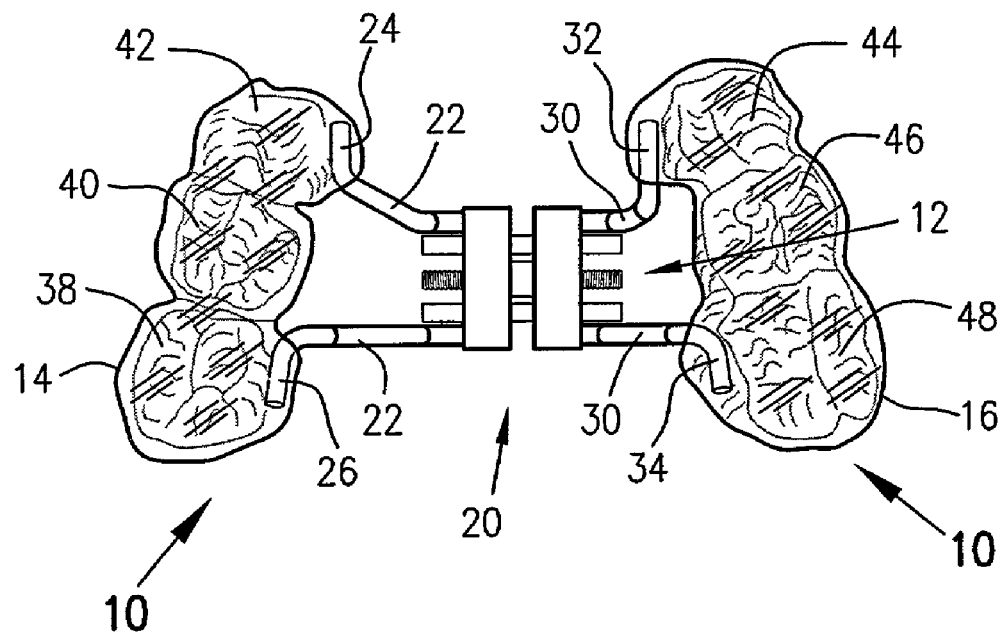
FIG. 1 is a diagrammatic plan view of the contoured palatal expander of the present invention.
Figure 2:
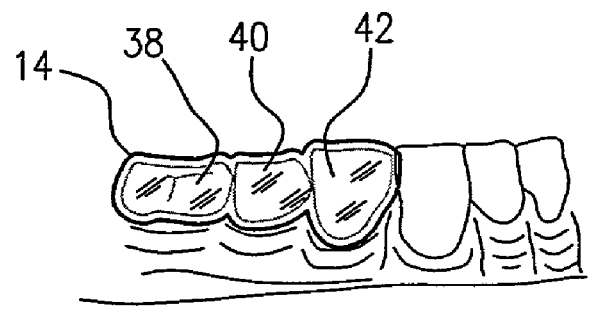
FIG. 2 is a diagrammatic elevational view of a portion of the contoured palatal expander of the present invention.

Referring now to FIG. 1, the palatal expander 10 of the present invention comprises an expansion screw portion 12 and tooth-engaging portions 14 and 16 at opposite ends of the expansion screw portion 12 and which are entirely of plastic material and are shaped to conform to and grasp selected ones of the patient's teeth. As shown in FIG. 1, expansion screw portion 12 includes a main body 20, a first extension 22 in the form of a pair of metal rods or wires having terminations 24, 26 and a second extension 30 in the form of a pair of metal rods or wires having terminations 32, 34. Teeth engaging portion 14 is secured to terminations 24, 26 and extends along the tops and sides of the three teeth 38, 40 and 42 shown in FIGS. 1 and 2. Similarly, teeth engaging portion 16 is secured to terminations 32, 34 and extends along the ends and sides of the three teeth 44, 46 and 48. In the embodiment shown, the terminations 24, 26 and 32, 34 are disposed at angles to the main body of the rod or wire from which they extend to enhance their connection to the respective teeth engaging portions 14, 16. The particular teeth and the number thereof which the portions 14 and 16 grasp are determined by the orthodontist.

The expansion screw portion 12 is illustrative of the many types of expansion screws and springs which can be included in the appliance 10 of the present invention. While each extension 22 and 30 shown in FIG. 1 comprises a pair of metal rods or wires each having an angled termination, alternatively each extension can comprise a single rod or wire with an angled extension at its end. By way of further example, in an illustrative appliance, reliable expansion progress was found to occur with an expansion screw sold under the registered trademark Forestadent.

Figure 3:
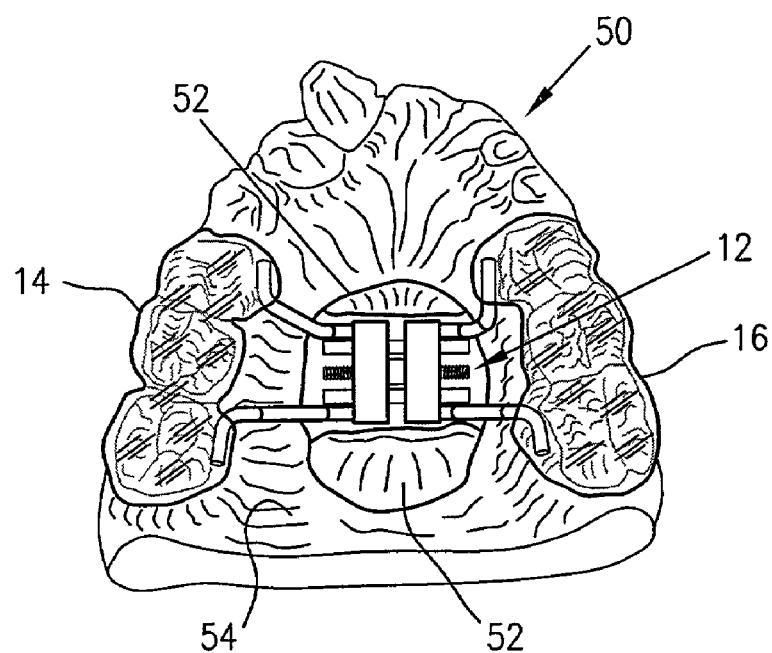
FIGS. 3 and 4 are perspective views illustrating a method of fabrication of the contoured palatal expander of the present invention.
Figure 4:
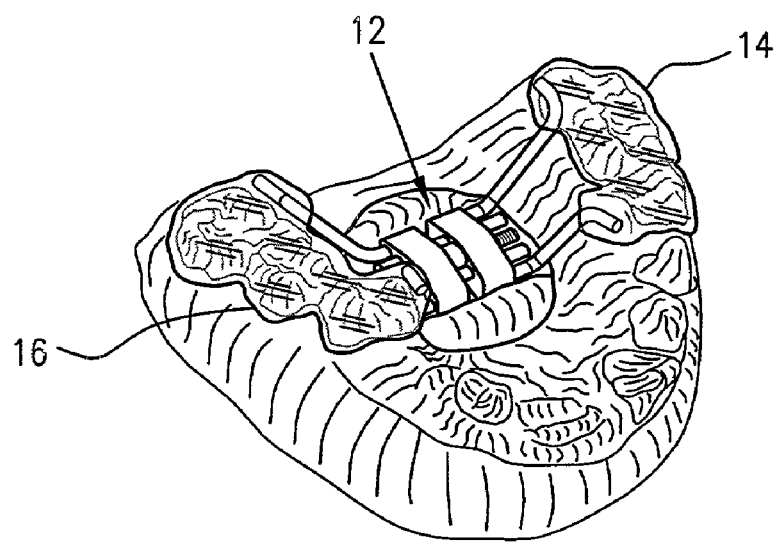

The expander 10 is fabricated by the method of the present invention in the following manner. A dental model of the patient's upper teeth, such as model 50 shown in FIGS. 3 and 4, is formed in a known manner. A quantity 52 of wax or like material is placed on the palatal portion 54 of the model. Material 52 supports expansion screw body 20, spacing it from the surface of model portion 54, and also spaces terminations 24, 26 and 32, 34 from the surfaces of the model teeth. Material 52 is selected to support expansion screw body 20 yet not bond to expander 10 or model 50 during formation of the appliance. In other words, material 52 is removable from expander 10 and model 50 after the fabrication process.

Next, a quantity of liquid acrylic material is brushed on or otherwise applied to terminations 24, 26 and 32, 34 which are spaced a small distance from the surfaces of the model teeth. Then a sheet, typically disc-shaped, of thermoplastic material, is placed over the model 50 in which the expansion screw portion 12 is supported. The model 50 containing expansion screw portion 12 with the plastic sheet thereover are placed in the receptacle of a dental appliance forming machine (not shown) such as the one commercially designated Biostar® and available from Great Lakes Orthodontics Ltd., Tonawanda, N.Y. The machine is operated in a known manner to thermally shape the disc of plastic material over the dental model 50 including the teeth thereof and over the expansion screw body 20, extensions 22, 30 and terminations 24, 26 and 32, 34. One form of plastic material found to be satisfactory is that commercially available from Great Lakes Orthodontics Ltd. under the designation Splint Biocryl® having a thickness of about 2 mm. For a more detailed description of the Biostar® machine and its method of operation, reference may be made to U.S. Pat. No. 3,768,164 issued Oct. 30, 1973 and entitled "Method of Making A Dental Appliance", the disclosure of which is incorporated herein by reference.

In comparison, some prior art fabrication techniques include the liquid and powder hand application of acrylic with subsequent curing. Fabrication according to the present invention does not use this but rather thermoplastic sheet material formed by heat and pressure over the expansion screw. A small amount of liquid and powder is immediately placed around the terminal ends and the expansion screw extensions.

Upon conclusion of operation of the machine and after the formed and shaped plastic material has cooled, the resulting product is removed from the machine. The plastic material is trimmed in a known manner so that only the teeth-engaging portions 14 and 16 of the plastic material remain. The terminations 24, 26 and 32, 34 are embedded in and thereby secured to the portions 14 and 16, respectively. The finished appliance 10 is best seen in FIGS. 3 and 4 residing in the model 50.

The appliance 10 is installed in the patient's mouth by placing the teeth-engaging portions 14, 16 onto the selected teeth which positions expansion screw portion 12 adjacent the roof of the patient's mouth. The portions 14, 16 are releasably attached or bonded to the patient's teeth by an improved cementation technique which will be described in detail presently. Then, using an expansion screw key or the like in a known manner, the expansion screw is advanced to tighten the portions 14 and 16 on the teeth they engage and to apply the prescribed amount of outward force against the teeth. Typically this is done in adjustment increments, each being effected by a quarter turn of the expansion screw in a known manner. When it is desired to remove appliance 10 from the patient's mouth, the expansion screw key or similar device is used to retract the expansion screw to loosen it from the portions 14 and 16 so that they can be released from the teeth and the appliance can be removed. By virtue of the tooth-engaging portions 14, 16 being entirely of plastic material, the foregoing installation and removal operations are performed in a manner which is quick and easy and relatively comfortable for the patient.

The contoured palatal expander 10 of the present invention is appropriate for patients in mixed or permanent dentition. It incorporates the thermoformed plastic to create the contoured caps 14 and 16 that are carefully molded to completely cover the lingual, occlusal and buccal surfaces of the anchor teeth. The appliance 10 provides a frameless design that allows the dental technician to finely trim the contour caps 14, 16 along the gingival margin or contour of each tooth, thereby eliminating plaque buildup and the possibility of gingivitis. The lab technician microetches the inner surface of the appliance caps in a manner which will be described to provide retention for the resin-modified glass ionomer cement used to releasably bond the caps 14 and 16 to the patient's teeth. Cementation of the appliance 10 to the patient's teeth requires no etching of the anchor teeth. The flexible nature of the contoured caps 14 and 16 facilitates their comfortable removal from the patient's teeth upon conclusion of the orthodontic treatment procedure.

The micro etching of the contoured appliance caps 14 and 16 and the cementation technique to releasably bond the caps to the patient's teeth now will be described. The micro etching of the inner surfaces of the caps 14, 16 is done to enhance the physical bond between the resin-modified glass ionomer cement and the plastic of the caps. The entire inside surfaces of both contoured caps 14 and 16, i.e., the tooth contacting surfaces, are abrasively etched by being blasted with a spray of aluminum oxide abrasive particles, preferably about 50 microns in size, using a micro etcher. By way of example, such a micro etcher is commercially available from Dannville Engineering. The micro-etching changes the appearance of the inner surfaces of the caps 14, 16 from a glossy to a mat-like finish.

Prior art methods for bonded palatal expanders used a cement which established a chemical bond to the appliance and to the teeth. This required more time consuming and laborious steps to prepare the surfaces of the patient's teeth. In particular, such steps included scouring the teeth surface with a pumice-containing instrument, acid etching the tooth enamel surfaces, rinsing, drying and isolating all surfaces (the isolation is to maintain absolutely dry surfaces), applying a liquid adhesive primer to the surface of the bondable expander, applying an adhesive paste to the inner surface of the bondable expander and placing the expander onto the anchor teeth until the adhesive has set.

The method of the present invention employs a resin-modified glass ionomer cement which establishes an exclusively physical bond to the plastic contoured caps 14, 16 and to the patient's teeth. There is no chemical bonding. This greatly simplifies the preparation of the tooth surfaces. In particular, the patient optionally brushes the teeth with water only, the light cured resin modified glass ionomer adhesive is mixed and applied with a fine brush and as a very thin coating to the previously micro-etched inner surfaces of the contoured plastic caps 14, 16 and then the appliance 10 is placed in the patient's mouth with the caps 14, 16 fitted on the anchor teeth and the adhesive is allowed to set.

The resin-modified glass ionomer cement establishes an exclusively physical bond, there being no chemical bonding, and the micro-etching of the inner surfaces of the contoured caps 14, 16 enhances the physical bond between the cement and the plastic material of the caps. The micro-etching can be performed as part of the fabrication of the appliance, or it can be performed as part of the procedure installing the appliance in the patient's mouth. By way of example, in an illustrative appliance and method, the resin modified glass ionomer adhesive can be GC Fuji Ortho™ self-cured orthodontic bonding adhesive.

Advantageously, the palatal expander 10 of the present invention is fabricated in about 60 minutes less time by lab technicians as compared to prior art expanders. The palatal expander 20 is bonded onto the patient's teeth in a one step process instead of three steps which reduces chair time approximately 20 minutes. Removal of the bonded palatal expander 10 is pain free whereas removal of the presently available prior art expanders can be quite painful. In particular, removal of the bonded expander is extremely easy due to the flex which occurs in the thermoplastic sheet material of portions 14 and 16 without the heavy metal wrap-around framework traditionally used. Patients are very comfortable because only a minimal force is applied to the teeth during removal. The palatal expander 10 of the present invention is much more hygienic and reduces the risk for decay and gingival inflammation.

Figure 5:
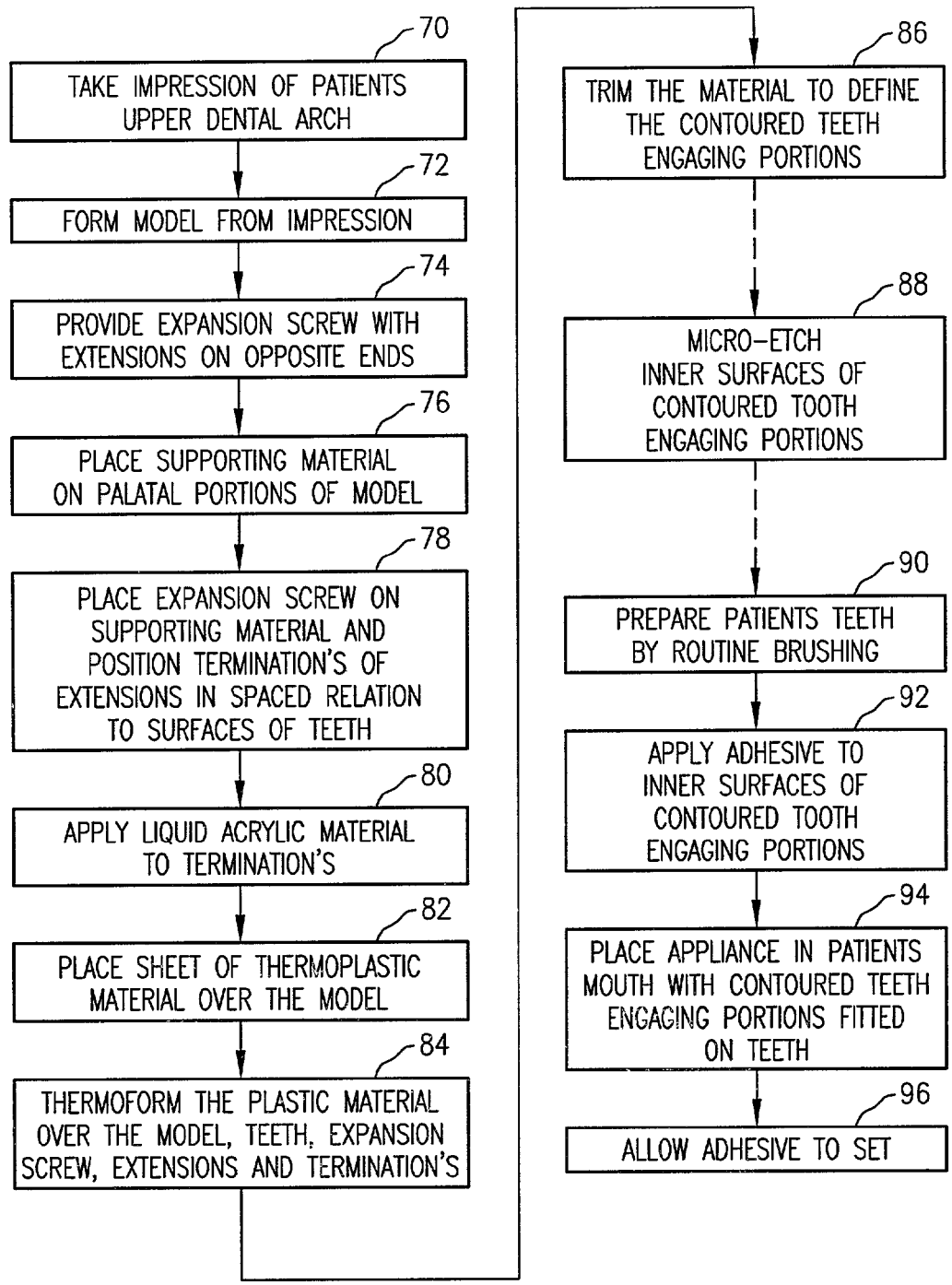
FIG. 5 is a flow diagram illustrating the method of the present invention.

The method of the present invention is further illustrated by the flow diagram of FIG. 5 wherein the steps 70–86 comprise fabrication of the appliance and the steps 90–96 comprise installation of the appliance in the patient's mouth. The micro-etching step 88 can be part of either fabrication or installation as indicated by the broken lines in FIG. 5.

Figure 6:
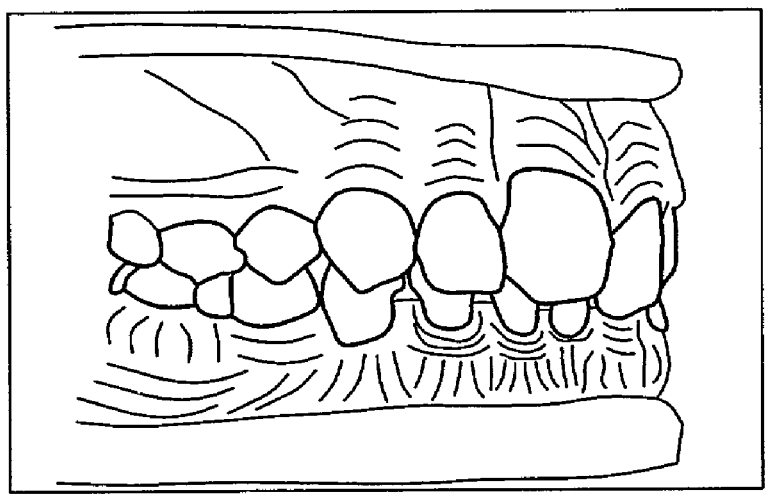
FIGS. 6 and 7 are diagrammatic views of a patient's teeth having deficient transverse maxillary width prior to use of the appliance of the present invention.
Figure 7:
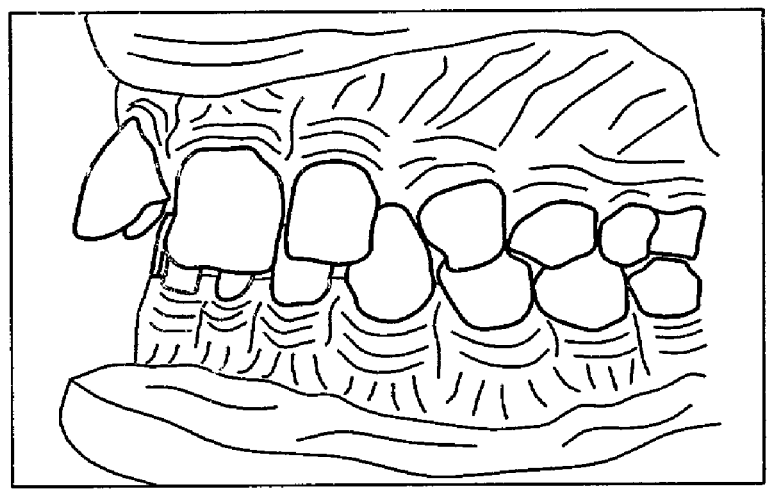

The present invention is illustrated further by the following example in the form of a patient case study. FIGS. 6 and 7 illustrate the patient's condition which is deficient transverse maxillary width. During the first appointment, about 20 minutes in duration, an upper arch alginate impression was taken, poured in orthodontic stone and then sent to a lab for fabrication of the appliance 10 according to the present invention. In the second appointment, approximately two weeks later and for about 20 minutes in duration, the appliance was inserted according to the following procedure. The patient's teeth were brushed with only water to remove any food or plaque. No other preparation or isolation of the teeth was required and the brushing with water could be omitted if the patient's teeth were sufficiently clean. With a sealant brush, a thin coating of resin-modified glass ionomer cement was painted into the microetched contour caps 14, 16 of the appliance. The intimate fit of the caps onto the teeth allows only a small amount of cement. The expander was placed on the anchor teeth and held for three minutes until the cement was set. The caps completely cover the tooth enamel for the purpose of preventing decalcification. This method of appliance delivery is very comfortable for patients and a major timesaver.

Complete verbal and written instructions were given to the patient/parent, advising them to turn the expansion screw the traditional rate of one full turn per day. It was recommended that the patient activate the screw a specific number of turns appropriate for the screw size (42 turns for an 11 mm screw). The patient was instructed to cease activations after completion of the turns. The patient was reappointed for appliance removal 13 weeks after initial insertion. This schedule provided seven weeks of active expansion followed by a six-week stabilization period. The patient was advised to use Listerine daily to reduce bacteria.

Figure 8:
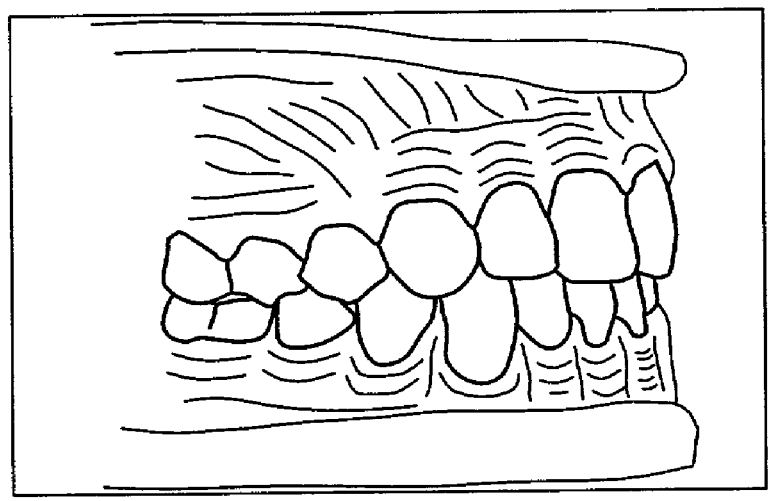
FIGS. 8 and 9 are diagrammatic views of the same patient's teeth after using the appliance of the present invention in a prescribed manner.
Figure 9:
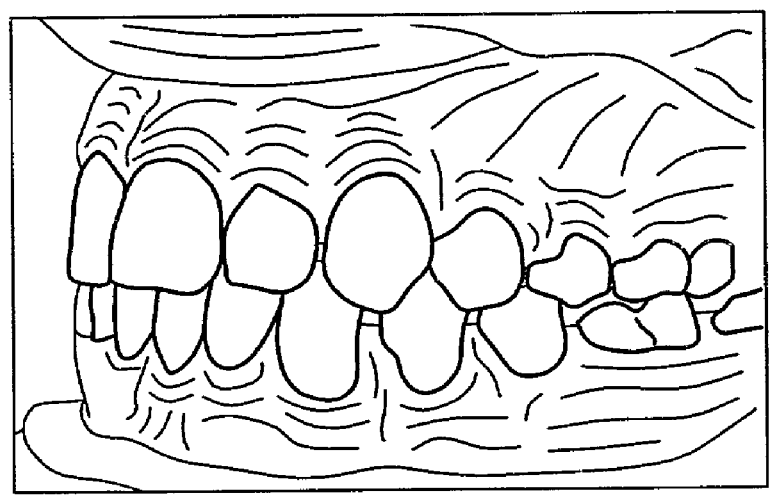

The third appointment, for appliance removal, occurred thirteen weeks after the second appointment and for a duration of about 20 minutes. Using Hamilton pliers, the buccal portion of each cap 14, 16 was lifted gently to break the seal on each tooth. The caps flex easily, allowing assistants to remove this appliance. Access at the gingival margin of the buccal surface and the ideal flex characteristics of the caps provide easy removal with less patient discomfort than traditional banded or bonded palatal expanders. The results of the treatment are illustrated in FIGS. 8 and 9.

What is claimed is:

1. A method of making a dental/orthodontic palatal expander appliance comprising:
   a) providing a model of the upper dental arch of a patient;
   b) providing an expansion screw having extensions leading from opposite ends thereof;
   c) supporting the expansion screw on the palatal portion of the model and positioning the ends of the extensions in closely spaced relation to selected ones of the teeth;
   d) providing a sheet of thermoplastic material;
   e) thermoforming the plastic material on the teeth and the ends of the extensions; and
   f) trimming the plastic material to define contoured tooth engaging portions which conform to and grasp selected ones of the teeth.

2. The method according to claim 1, wherein the expansion screw is supported by first applying a layer of supporting material to the palatal portion of the model and then placing the expansion screw on the supporting material.

3. The method according to claim 1, further including applying liquid acrylic material to the ends of the extensions prior to thermoforming the plastic material.

4. The method according to claim 1, wherein the trimming defines the contoured tooth engaging portions to extend along the gingival margin of the teeth.

5. The method according to claim 1, wherein the plastic material is formed and trimmed to shape and size each contoured tooth engaging portion to extend along the top and sides of the tooth which it engages.

6. The method according to claim 1, wherein the plastic material is formed and trimmed to shape and size each contoured tooth engaging portion to cover the lingual, occlusal and buccal surfaces of the tooth which it engages.

7. The method according to claim 1, further including abrasively etching the inner tooth contacting surfaces of the contoured tooth engaging portions.

8. A method for installing a dental/orthodontic palatal expander appliance comprising:
   a) providing an orthodontic palatal expander appliance comprising an expansion screw, extensions leading from opposite ends of the expansion screw and contoured tooth engaging portions fixed to the extensions and being of plastic material and shaped to conform to and grasp selected ones of a patient's teeth;
   b) applying a physically bonding orthodontic adhesive to the inner tooth-containing surfaces of the contoured tooth engaging portions; and
   c) placing the appliance in the patient's mouth with the contoured tooth engaging portions fitted on selected ones of the patient's teeth.

9. The method according to claim 8, further including abrasively etching the inner tooth contacting surfaces of the contained tooth engaging portions prior to applying the orthodontic adhesive thereto.

10. The method according to claim 9, wherein the abrasive etching is performed by a pressurized spray of abrasive particles each being about 50 microns in size.

11. The method according to claim 8, wherein the orthodontic adhesive is a resin modified glass ionomer adhesive.

12. The method according to claim 8, further including brushing the patient's teeth with liquid prior to applying the adhesive.

13. A dental/orthodontics palatal expander appliance comprising:
   a) an expansion screw having opposite ends;
   b) extensions leading from the opposite ends of the expansion screw; and
   c) contoured tooth engaging portions fixed to the extensions and being entirely of plastic material and being shaped to conform to and grasp selected ones of a patient's teeth, each contoured tooth engaging portion having an inner tooth contacting surface which is abrasively etched.

14. The appliance extensions and to and according to claim 13, wherein each contoured tooth engaging portion is shaped and sized to extend along and contact the top and sides of the tooth which it engages and to terminate substantially along the gingival margin of the tooth which it engages.

15. The appliance according to claim 13, wherein each contoured tooth engaging portion is shaped and sized to cover the lingual, occlusal and buccal surfaces of the tooth which it engages.

16. The appliance according to claim 13, wherein each extension comprises one or more members in the form of a rod and wherein the end of each member is embedded in a corresponding contoured tooth engaging portion.

17. The appliance according to claim 13, wherein the contoured tooth engaging portions are of thermoplastic material.

* * * * *